United States Patent [19]

Manner

[11] 4,390,710
[45] Jun. 28, 1983

[54] CATALYST SYSTEM FOR MANUFACTURING P-CHLOROPHENYL-N-METHYL CARBAMATE

[75] Inventor: James A. Manner, Akron, Ohio

[73] Assignee: PPG Industries, Inc., Pittsburgh, Pa.

[21] Appl. No.: 312,207

[22] Filed: Oct. 19, 1981

[51] Int. Cl.$^3$ .................. C07D 307/77; C07D 317/08; C07C 125/06

[52] U.S. Cl. .................................. 549/441; 549/452; 560/32; 560/115; 560/132; 560/134

[58] Field of Search ................. 560/132, 134, 115, 32; 260/346.22, 340.9 R; 549/441, 452

[56] References Cited

U.S. PATENT DOCUMENTS

| | | | |
|---|---|---|---|
| 2,776,196 | 1/1957 | Gysin et al. | 71/2.4 |
| 2,776,197 | 1/1957 | Gysin et al. | 71/2.4 |
| 2,812,247 | 11/1957 | Gysin et al. | 71/2.3 |
| 3,238,036 | 3/1966 | Herrett | 71/2.6 |
| 3,341,401 | 9/1967 | Kilsheimer et al. | 560/132 |
| 3,399,048 | 8/1968 | Herrett | 71/106 |
| 3,470,236 | 9/1969 | Hausweiler et al. | 560/132 |
| 3,597,472 | 8/1971 | Heiss et al. | 560/132 |

FOREIGN PATENT DOCUMENTS

| | | | |
|---|---|---|---|
| 611472 | 12/1960 | Canada | 560/32 |
| 984405 | 2/1976 | Canada | 260/469.6 |
| 2517774 | 10/1976 | Fed. Rep. of Germany . | |

OTHER PUBLICATIONS

"4-Dialkylaminopyridines As Highly Active Acylation Catalysts," by Gerhard Hofle et al., Angew. Chem. Int. Ed. Engl. 17, 569–570 and 573–583 (1978).

Primary Examiner—Donald B. Moyer
Assistant Examiner—Frederick W. Pepper
Attorney, Agent, or Firm—Irwin M. Stein; H. Lawrence Jones

[57] ABSTRACT

Aromatic esters of carbamic acid derivatives, e.g., p-chlorophenyl-N-methyl carbamate, are prepared by reaction of the corresponding aromatic alcohol, e.g., p-chlorophenol, and monoisocyanate, e.g., methyl isocyanate, in the presence of a catalytic amount of a combination of a 4-aminopyridine catalyst, e.g., 4-dimethylaminopyridine, and pyridine or methyl substituted pyridines. The product is substantially pure, having less than 0.80 weight percent allophanate ester by-product, e.g., p-chlorophenyl-N,N'-dimethyl allophanate, and less than 0.50 weight percent unreacted aromatic alcohol, e.g., p-chlorophenol. The reaction is readily controlled and characterized by the substantial absence of reflux. The product can be retained in the liquid state at reaction temperature for extended periods of time without significantly increasing the level of allophanate ester by-product.

13 Claims, No Drawings

CATALYST SYSTEM FOR MANUFACTURING P-CHLOROPHENYL-N-METHYL CARBAMATE

BACKGROUND OF THE INVENTION

The O-aryl esters of N-substituted carbamic acids include many compounds that have been found to be useful in agricultural applications. One such O-aryl carbamate is p-chlorophenyl-N-methyl carbamate. The aforesaid esters are prepared by the reaction of the corresponding aromatic alcohol, e.g., p-chlorophenol, with monoisocyanate, e.g., methyl isocyanate. The reaction between the aromatic alcohol and monoisocyanate can be accelerated by use of a tertiary amine, such as triethylamine or pyridine. The reaction can be conducted in the presence of an inert organic solvent; however, it can also be conducted in the absence of an extraneous inert organic solvent, as described in Canadian Pat. No. 984,405.

When conducted in the substantial absence of an extraneous solvent and with pyridine as the catalyst, the O-aryl carbamate product typically contains undesirable levels of allophanate by-product and the unreacted aromatic alcohol. Because the aforesaid O-aryl carbamates are used as agricultural chemicals, the levels of allophanate by-product and unreacted alcohol reactant therein is important for the reason that too high a level of such compounds can prevent governmental clearance of the use of the product in commerce.

It has now been discovered that O-aryl esters of substituted carbamic acids containing less than 0.8 weight percent allophanate by-product and 0.5 percent unreacted aromatic alcohol reactant can be prepared in the absence of an extraneous organic solvent by reacting the aromatic alcohol and monoisocyanate in the presence of a catalytic amount of the combination of a 4-aminopyridine catalyst, e.g., a 4-dialkylaminopyridine catalyst such as 4-dimethylaminopyridine, and a pyridine catalyst selected from pyridine, methylpyridines and dimethylpyridines. The aforesaid catalytic process provides numerous benefits; namely, (1) it proceeds readily to completion without significant refluxing of the isocyanate reactant and is, therefore, readily controlled; (2) it produces a substantially pure O-aryl carbamate product, which is satisfactory for commercial applications; (3) it involves less manufacturing cost than when a solvent is utilized; and (4) it permits the product to be maintained at reaction temperature for an extended time period without significantly affecting the level of by-product allophanate.

DETAILED DESCRIPTION

The utilization of O-aryl carbamates for agricultural applications is well known. Some changes or regulate the development of plant cells and thereby influence the growth of plants. The compound p-chlorophenyl-N-methyl carbamate has been found capable of extending the soil life of many organic herbicides such as isopropyl-N-(3-chlorophenyl) carbamate and isopropyl-N-phenyl carbamate even though the p-chlorophenyl-N-methyl carbamate appears to possess no significant herbicidal properties of its own.

Among the U.S. patents which describe O-aryl carbamates, there can be mentioned U.S. Pat. Nos. 2,776,196, 2,776,197, 2,812,247, 3,238,036, 3,399,048 3,597,472 and Canadian Pat. No. 984,405. Such patents describe a variety of O-aryl carbamates and the methods by which they can be produced. U.S. Pat. Nos. 2,776,196, 2,776,197 and 2,812,247 describe the art-recognized method of preparing carbamates by reaction of isocyanates with phenols. U.S. Pat. No. 3,238,036 describes the preparation of cyclohexenyl-N-methyl carbamate by the addition of methyl isocyanate to the corresponding alcohol, i.e., 3-cyclohexenyl methanol. The method described utilizes an inert organic solvent and a tertiary amine or organo tin catalyst.

U.S. Pat. No. 3,399,048 describes the preparation of substituted benzyl N-methyl carbamates, e.g., 3,4-dichlorobenzyl-N-methyl carbamates, by reacting a suitably substituted benzyl alcohol with methyl isocyanate. The use of an inert organic solvent and a tertiary amine or organo tin catalyst is described. U.S. Pat. No. 3,597,472 describes the preparation of indanyl-N-methyl carbamates by reacting an indanol with methyl isocyanate. The reaction is described as capable of being conducted with and without an inert solvent. Acceleration of the reaction is accomplished by the addition of a tertiary amine, e.g., triethylamine. Canadian Pat. No. 984,405 describes the preparation of p-chlorophenyl-N-methyl carbamate by reaction of p-chlorophenol with methyl isocyanate in the absence of an extraneous inert solvent in the presence of triethylamine or pyridine catalyst and also with no catalyst.

In the preparation of O-aryl carbamates in the absence of a solvent, the aromatic alcohol, monoisocyanate and catalyst are brought together and maintained at temperatures at which (1) the carbamate forming reaction proceeds, (2) the reaction medium (including the carbamate product) is liquid, and (3) the carbamate product does not decompose. The carbamate product is removed from the reactor in the molten state and recovered as a particulate solid, e.g., by prilling, flaking, etc. This procedure requires that the carbamate product be maintained above its melting point, e.g., at the temperature of the synthesis reaction, until the prilling or flaking operation is completed. At such temperatures, reaction of the carbamate product with unreacted monoisocyanate to form the allophanate by-product is favored.

The rate of allophanate by-product formation will vary with the catalyst used to accelerate the reaction. However, even when the rate of allophanate formation is low, the time required to process a batch of the molten product to a particulate solid can be unexpectedly lengthened because of the plugging of product transfer lines or operating difficulties with the solidification equipment, e.g., flaker, used. Such difficulties can result in a portion of the product containing higher levels of allophanate by-product than desired, e.g., the portions of the product removed from the reactor in the latter stages of the solidification step. The consequence of such factors is to limit the batch size of product that can be prepared at any one time or to tolerate higher levels than desired of allophanate in the product.

It has now been discovered that O-aryl carbamate product prepared by reaction of an appropriate aromatic alcohol with a monoisocyanate in the substantial absence of extraneous solvent can be maintained in a molten state for a significant period of time prior to recovery as a solid without developing objectionable levels of allophanate by-product by utilizing a combination of catalysts. In particular, it has been discovered that the aforementioned benefit is attained by use of a combination of a 4-aminopyridine catalyst, e.g., 4-dialkylaminopyridine, and a pyridine catalyst selected from pyridine, methylpyridines and dimethylpyridines.

The O-aryl carbamate product can be maintained in the liquid state at reaction temperatures without excessive allophanate by-product formation for at least 3 hours. From the evidence at hand, it is believed that the holding period at reaction temperatures can be extended to at least six, e.g., 12 hours. This permits the product to be analyzed before being solidified and further permits the molten product to be stored in a hold tank which feeds the solidification step, thereby permitting larger batches of product to be produced and freeing the reactor for use in preparing further product.

O-aryl carbamate product prepared with the aforesaid combination of catalysts typically contains less than 0.8 and 0.5 weight percent of allophanate by-product and unreacted aromatic alcohol reactant respectively even after being maintained in the molten state for six hours at reaction temperatures. Further, the reaction proceeds smoothly to completion without significant refluxing of monoisocyanate reactant. Typically, the amount of allophanate by-product initially in the carbamate ester product, i.e., upon completion of the alcohol-isocyanate reaction, is less than about 0.5 weight percent, often less than 0.2 weight percent. Similarly, the amount of unreacted aromatic alcohol in the carbamate ester product is typically less than 0.2 weight percent, often less than 0.1 weight percent upon completion of the reaction. Allophanate and unreacted aromatic alcohol initial levels in the carbamate ester of 0.1 and 0.05 weight percent respectively have been attained under the most preferred process conditions.

4-aminopyridines useful as catalysts in the above-described reaction can be represented by the following graphic formula:

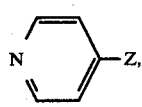
(1)

wherein Z is selected from the group consisting of

pyrrolidino, piperidino, and morpholino, and R' and R" are each selected from the group consisting of hydrogen, branched and straight chain $C_1$-$C_6$ alkyl and $C_3$-$C_7$ cycloalkyl. Such 4-aminopyridines can be represented further by the following graphic formulae:

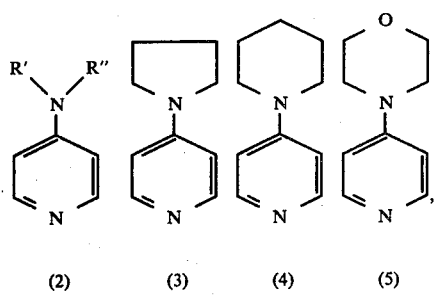
(2)   (3)   (4)   (5)

which formulae depict 4-aminopyridine or 4-dialkylaminopyridines, 4-pyrrolidinopyridine, 4-piperidinopyridine and 4-morpholinopyridine.

Examples of 4-aminopyridines include: 4-aminopyridine, 4-methylaminopyridine, 4-dimethylaminopyridine, 4-ethylaminopyridine, 4-diethylaminopyridine and analogous compounds wherein the alkyl group(s) are n-propyl, isopropyl, n-butyl, s-butyl, t-butyl, amyl, and hexyl; 4-cyclopropylaminopyridine, 4-cyclobutylaminopyridine, 4-cycloamylaminopyridine, 4-cyclohexylaminopyridine, 4-cyclopropylmethylaminopyridine, 4-cyclopropylethylaminopyridine, 4-pyrrolidinopyridine, 4-piperidinopyridine and 4-morpholinopyridine.

The synthesis of 4-dialkylaminopyridines and their use as an acylation catalyst is described in the article, "4-Dialkylaminopyridine As Highly Active Acylation Catalysts", by Gerhard Hofle et al, Angew. Chem. Int. Ed. Engl. 17 569–583 (1978). The aforesaid article does not describe the use of 4-dialkylaminopyridines as a catalyst for the reaction between an aromatic alcohol and a monoisocyanate.

As described in the aforesaid Hofle et al article, 4-aminopyridines, e.g., dimethylaminopyridine, can be prepared by the reaction of N,N-dialkylformamide, e.g., N,N-dimethylformamide, with 1-(4-pyridinio) pyridinium dichloride at 140°-160° C. The latter compound is prepared by the reaction of thionyl chloride with pyridine. The analogous reaction of the pyridinium dichloride with N-formylpyrrolidine yields 4-pyrrolidinopyridine; with N-formylpiperidine yields 4-piperidinopyridine; and with N-formylmorpholine yields 4-morpholinopyridine.

Pyridine catalyst used in combination with the aforesaid 4-aminopyridine is selected from the group consisting of pyridine, methylpyridines and dimethylpyridines. As the methylpyridine there can be used 2-methylpyridine (alpha-picoline), 3-methylpyridine (beta-picoline), 4-methylpyridine (gamma-picoline) or mixtures of such methylpyridines. As the dimethylpyridines (lutidine) there can be used 2,3-, 2,4-, 2,5-, 2,6-, 3,4-, or 3,5-dimethylpyridine or mixtures of such dimethylpyridines.

The amount of 4-aminopyridine and pyridine compound used to accelerate the aromatic alcohol-isocyanate reaction is that amount which accelerates the reaction to substantial completion in a reasonable time frame, i.e., a catalytic amount. Typically, between about 0.01 and about 0.5 weight percent each of 4-aminopyridine and pyridine compound, basis the aromatic alcohol compound, is used as the catalyst. More commonly, between 0.05 and about 0.1, e.g., 0.075, weight percent each of the 4-aminopyridine and pyridine catalyst is used. In the preparation of p-chlorophenyl-N-methyl carbamate, between about 0.01 and 0.10 weight percent each of 4-aminopyridine and pyridine compound are typically used.

The weight ratio of 4-aminopyridine to pyridine catalyst can vary from about 5:1 to 1:5, more usually from about 2:1 to 1:2. Preferably, the weight ratio will range from about 1:1 to 2:1, e.g., 1.3:1 to 1.5:1.

The actual amount of 4-aminopyridine and pyridine catalyst used will vary depending on the purity of the reactants, i.e., monoisocyanate and aromatic alcohol. It has been observed that the purity of the starting reactants not only effects the purity of the product but also the amount of catalyst required because some impurities in the reactants are acidic. Such acidic impurities neutralize or otherwise combine or complex with a portion of the catalyst, thereby reducing the actual mount of, for example, 4-aminopyridine available to function as a catalyst. For example, analysis of some commercial methyl isocyanate material has revealed a small but significant acidity level (as hydrochloric acid) and hydrolyzable chloride. The presence of such acidic impurities takes on significance when the amount of catalyst used (which also is small) is considered. Thus, the amount of catalyst used must take into account the portion of catalyst that may be consumed by combining with acidic impurities. The proper amount of catalyst required can be readily ascertained by conducting trial laboratory runs with samples of the reactants to be used.

The monoisocyanate used in the reaction with the hydroxy aromatic compound can be represented by the following general formula:

$$R'''\text{—}N\text{=}C\text{=}O \quad (6)$$

wherein R''' is selected from the group consisting of straight or branched chain $C_1-C_3$ alkyl, cyclohexyl and phenyl. Examples of such monoisocyanates include methyl isocyanate, ethyl isocyanate, n-propyl isocyanate, isopropyl isocyanate, cyclohexyl isocyanate and phenyl isocyanate.

Aromatic alcohols that can be used in the above-described reaction to form O-aryl carbamates include compounds obtained by adding a hydrogen to the radical formed by cleaving art-recognized O-aryl carbamates between the ether oxygen and carbonyl group. Thus, any of the corresponding hydroxy aromatic alcohols used to prepare aryl esters of N-substituted carbamic acids described in the prior art can be used. As used in the specification and claims, the term aromatic alcohol, hydroxy aromatic or like terms are, unless indicated to the contrary, intended to mean and include hydroxy aryl compounds, e.g., monohydroxy aryl compounds, that contain a hydroxyl group attached to an aromatic or carbon ring, e.g., phenol, cresols, xylenols, or to a side chain, e.g., benzyl alcohol, tolyl alcohol, xylyl alcohol. Typically, the aromatic alcohols can be represented by the following general formula:

$$R\text{—}OH \quad (7)$$

wherein R is phenyl, substituted phenyl, e.g., halosubstituted phenyl, naphthyl, halosubstituted naphthyl, benzofuranyl, lower alkyl ($C_1-C_4$) substituted benzofuranyl, benzyl and substituted, e.g., halosubstituted, benzyl radicals.

More particularly, the aromatic alcohols that can be used can be represented by the following graphic formulae:

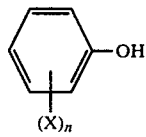 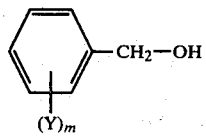

(8)     (9)

wherein X is hydrogen, halogen, $C_1-C_8$ alkyl, $C_1-C_4$ alkoxy, $C_1-C_4$ alkylthiol, $C_1-C_4$ dialkylamino, nitro, 1,3-dioxolanyl, 4,5-di($C_1-C_4$) alkyl-1,3-dioxolanyl and n is an integer of from 1 to 3; Y is selected from the group consisting of halogen and nitro and m is an integer of from 1 to 2. More particularly, the hydroxy aromatic compounds of formula (8) can be represented by the graphic formula:

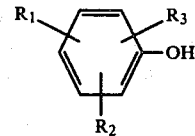

(10)

wherein $R_1$ is selected from the group consisting of hydrogen, halogen, $C_1-C_5$ alkyl, $C_1-C_3$ alkoxy, $C_1-C_3$-alkylthiol and nitro, and $R_2$ and $R_3$ are each selected from the group consisting of hydrogen and $C_1-C_5$ alkyl.

The halogen substituent in any of the above formulae can be chlorine, fluorine, bromine or iodine; but is typically chlorine or bromine. The hydroxy aromatic compounds described hereinabove, are commercially available or can be prepared by art-recognized techniques.

Examples of hydroxy aromatic compounds represented by the above structural formulae include: phenol, p-chlorophenol, o-chlorophenol, 2-sec-butylphenol, m-(1-ethylpropyl)phenol, m-(1-methylbutyl)-phenol, 3-dimethylaminomethyleneiminophenol, o-(1,3-dioxolan-2-yl)phenol, o-(4,5-dimethyl-1,3-dioxolan-2-yl)phenol, alpha naphthol, chloronaphthol, 3,4-dimethylphenol, 3-methyl-5-isopropylphenol, 3,5-di-t-butylphenol, o-isopropoxyphenol, 4-dimethylamino-3-methylphenol, 3,4,5-trimethylphenol, 4-dimethylamino-3,5-dimethylphenol, benzyl, tolyl and xylyl alcohol. Further examples of hydroxy aromatic compounds are described in the literature. See, for example, the hydroxy aromatic compounds described in U.S. Pat. Nos. 2,776,197 and 2,812,247, as well as the hydroxy aromatic derivatives of the O-aryl carbamates described in such patents. Such hydroxy aromatic compounds are incorporated herein by reference.

In accordance with the process described herein, the reaction of the hydroxy aromatic and monoisocyanate compounds is conducted in the substantial absence of an extraneous solvent, e.g., an inert organic solvent. The only materials present in amounts sufficient to serve as a solvent for the reaction system are the reactant and the reaction products. Although minor amounts of low boiling inert impurities can be present, the solvent effect of these impurities is negligible.

The relative amount of reactant materials used can vary; but, commonly they are used in substantially stoichiometric amounts, i.e., about a 1:1 mole ratio. In order to achieve substantially complete reaction and minimize the amount of unreacted aromatic alcohol in the carbamate product, it is common to utilize a slight excess of the monoisocyanate, e.g., methyl isocyanate. Typically the excess of monoisocyanate is 8 mole percent or less, preferably between about 2 and about 5, e.g., 3, mole percent. Thus, the mole ratio of isocyanate to aromatic alcohol can vary between about 1:1 and about 1.08:1, e.g., between about 1:1 or 1.03:1 and about 1.05:1.

In carrying out the reaction, the reactants are brought together in a suitable reaction vessel in the presence of the aforedescribed 4-aminopyridine and pyridine catalysts and at temperatures above the melting point of the reactants. The order of reactant introduction is not critical, i.e., the reactants can be added in any order or simultaneously; however, it is customary to add the isocyanate to the liquid hydroxy aromatic compound containing the catalyst mixture because of melting point considerations. Thus, in the case of p- chlorophenol and methyl isocyanate, the relationship of the respective melting points is in the order of: methyl isocyanate <p-chlorophenol <p-chlorophenyl-N-methyl carbamate.

The melting points of the reactants and products have a bearing on the reaction temperature. At the beginning of the reaction when little or no carbamate, e.g., p-chlorophenyl-N-methyl carbamate, is present, the reaction temperature can be as low as the melting point of the hydroxy aromatic compound, e.g., p-chlorophenol. As the reaction progresses and O-aryl carbamate ester is produced, the liquidus temperature of the reaction medium increases and higher temperatures are necessary to maintain the system in the liquid state. The reaction temperature will, of course, vary depending on the particular carbamate produced and the melting points of the hydroxy aromatic compound and the carbamate ester. In conducting the reaction, care should be observed that the reaction mixture is maintained in a liquid state and the reaction temperature not permitted to reach a level at which the carbamate ester product degrades.

Typically, reaction temperatures will range between about 35° C. and about 150° C. For the reaction of p-chlorophenol with methyl isocyanate, reaction temperatures usually range between about 70° C. and about 125° C., e.g., between 70° C. and 115° C. or 120° C. Temperatures above 125° C., e.g., 130° C., favor the more rapid formation of the allophanate by-product in the case of p-chlorophenyl-N-methyl carbamate, and, therefore, are to be avoided.

Solidification of the carbamate product can be accomplished by any method customarily used for this purpose with other similar molten materials. Among these are casing, prilling or flaking. Flaking is preferred. The molten products can also be solidified by pouring them into water which, preferably, but not necessarily, is agitated.

The reaction is conducted with agitation sufficient to turn over and thoroughly mix the liquid contents of the reaction mixture. Insufficient agitation can result in incomplete reaction, refluxing of the monoisocyanate and formation of solids in the reactor.

As indicated, the O-aryl carbamate product produced in accordance with the present process is substantially pure, i.e., contains less than 0.8 weight percent, often less than 0.5 weight percent allophanate (the product produced by reaction of the carbamate ester with an additional mole of isocyanate) and less than 0.5 weight percent, often less than 0.1 weight percent, unreacted hydroxy aromatic reactant. Parachlorophenyl-N-methyl carbamate produced in accordance with the present process has been found to initially contain less than 0.1 weight percent p-chlorophenyl-N-N'-dimethyl allophanate and less than 0.1 weight percent p-chlorophenol upon completion of the reaction, e.g., when all the isocyanate has been added to the reactor. If desired, the carbamate ester can be purified further by dissolving it in an inert solvent and recrystallizing the carbamate from the solvent. In order to avoid any possibility of thermal degradation, the dissolving and recrystallization should be conducted at temperatures below that at which such degradation can occur, which in the case of p-chlorophenyl-N-methyl carbamate is less than 115° C. e.g., 100° C. Inert solvents useful for performing recrystallization include: methyl chloroform, methylene chloride, acetone, ethanol and a mixture of ethanol and water.

The present process is more particularly described in the following examples, which are intended as illustrative only since numerous modifications and variations therein will be apparent to those skilled in the art. In the following examples, the process of the present invention is exemplified by the reaction of p-chlorophenol with methyl isocyanate to form p-chlorophenyl-N-methyl carbamate. In such examples, analysis of the product was performed by high performance liquid chromatography (HPLC), unless otherwise indicated. As further exemplification of the present process, the hydroxy aromatic compounds and monoisocyanate compounds described above can be substituted for the p-chlorophenol and methyl isocyanate respectively in the examples and expect to obtain the corresponding O-aryl carbamates.

In the following examples, essentially the same experimental procedure was followed except for changes in the type and amount of catalyst and the amount of excess monoisocyanate. Minor variations in the preheat temperatures were a result of fluctuations in the heat source and are not considered experimentally significant as the reaction temperature was in the 115°–120° C. range. Variations in the methyl isocyanate addition time were a result of attempts to conduct the reaction with no or a minimum of reflux of methyl isocyanate and without excessive exotherm and are not considered experimentally significant.

EXAMPLE I

To a three hundred milliliter (ml), four-necked, baffled, round bottom reaction flask, equipped with a passivated stainless steel paddle stirrer and shaft, thermometer, bottom stopcock and addition funnel was added 128.6 grams (1.0 mole) of p-chlorophenol (PCP) from commercial source A, 0.065 grams (0.05 weight percent, basis PCP) of 4-dimethylaminopyridine (DMAP), and 0.065 grams (0.05 weight percent, basis PCP) of pyridine. Before addition of the PCP, the reaction flask was heated and swept with nitrogen to drive out any moisture present in the flask. To the addition funnel was added 59.9 grams (1.05 moles, 62.4 ml), i.e., a 5 mole percent excess, of methyl isocyanate from commercial source A. The PCP-catalyst mixture was stirred and heated to 75° C. at which time dropwise addition of he methyl isocyanate (MIC) into the reaction flask was started. The MIC was added over a period of 30 minutes. The temperature of the reaction mixture rose rapidly to 119° C. in the first ten minutes of MIC addition and was controlled at between 115° C. and 120° C. throughout addition of the remaining methyl isocyanate and during post stirring by blowing cool air onto the reaction flask. There was a slight amount of refluxing of methyl isocyanate observed with 3.5 ml of methyl isocyanate remaining to be added. This reflux stopped when all of the isocyanate had been added.

After completing addition of the methyl isocyanate, the reaction mixture was stirred and maintained at temperature (115°–120° C.) for 98 minutes. Samples were removed periodically by means of the bottom stopcock. The molten product samples were drained into a Pyrex container where they rapidly solidified. Samples were submitted for HPLC analysis. Results are tabulated in Table I.

TABLE I

| Catalyst, % | Hold Time at 115-120° C. min. | HPLC Analysis, Wt. % | | | |
|---|---|---|---|---|---|
| | | PC[1] | 2,6-PC[2] | PCP[3] | ALP[4] | Assay[5] |
| Pyridine, 0.05 | 4 | 0.04 | 0.30 | 0.11 | 0.28 | 99.3 |
| DMAP[6], 0.05 | 33 | 0.06 | 0.36 | Trace | 0.34 | 99.2 |
| | 67 | 0.06 | 0.24 | 0.07 | 0.33 | 99.3 |
| | 98 | 0.06 | 0.26 | 0.08 | 0.33 | 99.3 |

[1]PC - phenylcarbamate from phenol impurity in PCP
[2]2,6-dichlorophenylcarbamate from 2,6-dichlorophenol impurity in PCP
[3]PCP - parachlorophenol
[4]ALP - p-chlorophenyl-N,N'—dimethylallophanate
[5]Assay calculated by difference
[6]4-Dimethylaminopyridine The data of Table I show that after about 1½ hours at 115°–120° C., the amount of unreacted p-chlorophenol and p-chlorophenyl-N,N'-dimethylallophanate remained substantially at the same levels as existed at the completion of the reaction.

EXAMPLE II

The procedure of Example I was followed using p-chlorophenol from commercial source B and methyl isocyanate from commercial source C. The p-chlorophenol was 99.5% pure. The methyl isocyanate was used in a 3 mole percent excess. The phenol-catalyst mixture was heated to 75° C. before initiating addition of the methyl isocyanate, which was added slowly over a period of 32 minutes. There was no refluxing of methyl isocyanate during the entire run. After completing the methyl isocyanate addition, the reaction mixture was stirred and maintained at temperature (115°–120° C.) for 185 minutes. Samples were taken during this post reaction holding period at 5, 65, 125 and 185 minutes and submitted for HPLC analysis. Results are tabulated in Table II.

EXAMPLE III

The procedure of Example II was followed except that 0.10 weight percent of 4-dimethylaminopyridine was used as the only catalyst and the methyl isocyanate was added slowly over a period of 31 minutes. There was no refluxing of methyl isocyanate during the entire run. Samples were taken during the post reaction holding period at 3, 68, 155 and 215 minutes. Results are tabulated in Table II.

TABLE II

| Example No. | Catalyst, % | Hold Time at 115-120° C. min. | HPLC Analysis, Wt. % | | | |
|---|---|---|---|---|---|---|
| | | | PC[1] | PCP[3] | ALP[4] | Assay[5] |
| II | Pyridine, 0.05 | 5 | N.D.[7] | N.D. | N.D. | 99.9 |
| | DMAP[6], 0.05 | 65 | N.D. | N.D. | 0.23 | 99.8 |
| | | 125 | N.D. | N.D. | 0.26 | 99.7 |
| | | 185 | N.D. | N.D. | 0.28 | 99.7 |
| III | DMAP, 0.10 | 3 | N.D. | N.D. | 0.14 | 99.9 |
| | | 68 | N.D. | N.D. | 0.42 | 99.6 |
| | | 155 | N.D. | N.D. | 0.95 | 99.0 |
| | | 215 | N.D. | N.D. | 0.97 | 99.0 |

[1,3-6]. See Footnotes in Table I.
[7]N.D. - Not Detected

The data of Table II show that in Example II after 3 hours at 115°–120° C. the amount of unreacted p-chlorophenol in the product was not detected and allophanate remained substantially constant at about 0.28 percent. In Example III, when 4-dimethylaminopyridine was used as the only catalyst (at 0.10 wt. %), the allophanate level gradually increased to about 0.95–0.97 weight percent in three hours.

EXAMPLE IV

The procedure of Example II was followed except that a different lot of p-chlorophenol from commercial source B from that used in Example II was employed. Further, the p-chlorophenol had been in storage for about 7 months. In addition, 0.075 weight percent of each of 4-dimethylaminopyridine and pyridine was used to accelerate the reaction. The methyl isocyanate was added slowly over a period of 28 minutes. No reflux of the isocyanate was observed during the entire period of its addition. Samples were taken at 5, 75, 135 and 195 minutes during the post reaction holding period. After 3¼ hours, the level of p-chlorophenol jumped from 0.19 (at 2¼ hours) to 0.42 weight percent,—an atypical result. Data obtained are tabulated in Table III.

EXAMPLE V

Because of the results obtained in Example IV, the procedure was repeated except that 0.05 weight percent of each catalyst was used. The methyl isocyanate was added slowly over a period of 37 minutes. Samples were taken at 7, 67, 127 and 187 minutes. Results are tabulated in Table III.

EXAMPLE VI

The procedure of Examples IV and V was followed except that 0.10 weight percent of dimethylaminopyridine was used as the only catalyst. The methyl isocyanate was added slowly over a period of 29 minutes. No refluxing of the methyl isocyanate was observed during the period of its addition. Samples were taken at 5, 70, 125 and 190 minutes during the post reaction holding period. Results are tabulated in Table III.

TABLE III

| Example No. | Catalyst, % | Hold Time at 115-120° C. min. | HPLC Analysis, Wt. % | | | |
|---|---|---|---|---|---|---|
| | | | PC[1] | PCP[3] | ALP[4] | Assay[5] |
| IV | Pyridine, 0.075 | 5 | 0.08 | <0.05 | <0.10 | 99.9 |
| | DMAP[6], 0.075 | 75 | 0.09 | 0.19 | 0.21 | 99.5 |
| | | 135 | 0.09 | 0.19 | 0.40 | 99.7 |
| | | 195 | 0.09 | 0.30 | 0.53 | 99.1 |
| V | Pyridine, 0.05 | 7 | 0.10 | 0.05 | 0.07 | 99.8 |
| | DMAP, 0.05 | 67 | 0.09 | 0.06 | 0.10 | 99.8 |
| | | 127 | 0.10 | 0.06 | 0.16 | 99.7 |
| | | 187 | 0.10 | 0.11 | 0.21 | 99.6 |
| VI | DMAP, 0.10 | 5 | 0.08 | N.D. | N.D. | 99.9 |
| | | 70 | 0.08 | 0.21 | 0.27 | 99.4 |
| | | 125 | 0.09 | 0.39 | 0.47 | 99.1 |
| | | 190 | 0.09 | 0.51 | 0.68 | 98.7 |

[1,3-6]See footnotes in Table I

The large increase in the PCP level in the product of Examples IV and VI is anomalous to a significant number of other experiments using the same catalyst system and, therefore, is believed to be a result of product decomposition due to impurities formed during storage of the p-chlorophenol. A fresh supply of methyl isocyanate and p-chlorophenol was obtained for further experiments.

EXAMPLE VII

The procedure of Example I was followed except that the p-chlorophenol was obtained from commercial source D and the methyl isocyanate from commercial source C. The methyl isocyanate was used in 3 mole percent excess and added slowly to the phenol-catalyst mixture over 30 minutes. No reflux was observed during addition of the isocyanate. The catalyst mixture added to the p-chlorophenol was 0.075 weight percent of 4-dimethylaminopyridine and 0.05 weight percent pyridine (basis PCP).

After addition of the methyl isocyanate, the reaction mixture was maintained at about 117°–119° C. while being stirred for 360 minutes. Samples were taken at 3, 60, 200, and 360 minutes. Results are tabulated in Table IV.

TABLE IV

| Catalyst, % | Hold Time at 117-119° C. Min. | HPLC Analysis, Wt. % | | | | | |
|---|---|---|---|---|---|---|---|
| | | $PC^1$ | $2,6-PC^2$ | $PCP^3$ | $2,4-PC^7$ | $ALP^4$ | $Assay^5$ |
| Pyridine, 0.05 | 3 | 0.14 | 0.10 | 0.03 | 0.79 | N.D. | 98.9 |
| $DMAP^6$, 0.075 | 60 | 0.14 | 0.09 | Trace | 0.55 | 0.12 | 99.1 |
| | 200 | 0.15 | 0.15 | 0.18 | 0.66 | 0.19 | 98.7 |
| | 360 | 0.15 | 0.15 | 0.28 | 0.65 | 0.26 | 98.5 |

$^{1-6}$See footnotes in Table I.
$^7$2,4-dichlorophenylcarbamate from 2,4-dichlorophenol impurity in PCP.

The data of Table IV show that the combination of 4-dimethylaminopyridine and pyridine allow the carbamate product produced by reaction of methyl isocyanate and p-chlorophenol to be retained for as long as 6 hours at 115°–120° C. without excessive formation of allophanate by-product.

The following examples are included for purposes of comparison.

EXAMPLE VIII

The procedure of Example I was followed except that the p-chlorophenol was obtained from commercial source, D, 0.10 weight percent (basis PCP) of pyridine (PY) was used as the only catalyst, and the reaction flask was equipped with a Teflon blade stirrer and glass shaft. The preheat temperature of the phenol-catalyst mixture was 78° C. and the methyl isocyanate was added slowly over 34 minutes. Results are tabulated in Table V. The results show that while fairly low p-chlorophenol levels were obtained after 1½ hours of hold time with the use of pyridine, the allophanate levels reach 0.90 weight percent or above. A moderate amount of methyl isocyanate refluxing was also observed during the reaction.

EXAMPLE IX

The procedure of Example VIII was followed except that the catalyst was 2-methylpyridine (PIC) instead of pyridine, the preheat temperature of the phenol-catalyst mixture was 70° C. and the methyl isocyanate was added slowly over 32 minutes. Results are tabulated in Table V. The results show that allophanate levels were about 0.85 weight percent after 1½ hours of hold time and relatively high levels of p-chlorophenol (1.5 weight percent) were present in the carbamate product. A small amount of methyl isocyanate refluxing was observed during the reaction.

EXAMPLE X

The procedure of Example VIII was followed except that the catalyst was 2,6-dimethylpyridine (LUT), the preheat temperature of the phenol-catalyst mixture was 73° C. and the methyl isocyanate was added slowly over 33 minutes. Results are tabulated in Table V. These results show that although relatively low levels of p-chlorophenol were observed in the carbamate product after 1½ hours hold time, the level of allophanate therein was found to be above 0.9 weight percent. Moreover, extensive refluxing of methyl isocyanate was observed during the reaction.

TABLE V

| Example No. | Catalyst % | Hold Time at 115-120° C. | | Analysis % | | | |
|---|---|---|---|---|---|---|---|
| | | Hr. | Min. | PCP | ALP | Assay | Unknowns |
| VIII | $PY,^{1b,2}$ 0.10 | 0 | 30 | 0.28 | 0.97 | 98.7 | 0.09 |
| | | 1 | 0 | 0.52 | 0.93 | 98.5 | 0.10 |
| | | 1 | 30 | 0.25 | 0.90 | 98.8 | 0.08 |
| IX | $PIC,^{1a,2}$ 0.10 | 0 | 30 | 1.5 | 0.83 | 97.5 | 0.13 |
| | | 1 | 0 | 1.6 | 0.85 | 97.4 | 0.14 |
| | | 1 | 30 | 1.5 | 0.85 | 97.5 | 0.14 |
| X | $LUT,^{1c,2}$ 0.10 | 0 | 30 | 0.14 | 0.93 | 98.8 | 0.08 |
| | | 1 | 0 | 0.25 | 0.91 | 98.8 | 0.08 |
| | | 1 | 30 | 0.17 | 0.93 | 98.8 | 0.09 |

$^1$At the End of the MIC Addition:
$^a$Small amount of refluxing
$^b$Moderate refluxing
$^c$Extensive refluxing
$^2$Abbreviation:
PY - Pyridine
PIC - 2 Methylpyridine (α-picoline)
LUT - 2,6-Dimethylpyridine (2,6-Lutidine)
PCP - p-chlorophenol
ALP - p-chlorophenyl-N,N'—dimethyl allophanate The results of Table V show that none of the catalysts used in Examples VIII-X produce a p-chlorophenyl-N-methyl carbamate product which contains low levels of both p-chlorophenol and allophanate after 1½ hours of hold time at 115°–120° C. High levels of p-chlorophenol in the carbamate product show poor catalyst performance for finishing the phenol-isocyanate reaction. High levels of allophanate in the carbamate product show that the catalyst enhances the reaction of the isocyanate with the carbamate. In all cases, refluxing of methyl isocyanate was observed during the reaction making the reaction more difficult to control. In Example VIII moderate refluxing was observed and in Example X extensive refluxing was observed.

EXAMPLE XI

The procedure of Example I was followed using p-chlorophenol and methyl isocyanate obtained from commercial source A and using 0.13 grams (0.10 weight percent, basis PCP) of pyridine as the catalyst. Analysis of the PCP revealed the following: p-chlorophenol, 99.5%; 2,6-dichlorophenol, 0.29%; o-chlorophenol, trace; 2,4-dichlorophenol, 0.05%; phenol, 0.15%. The phenol-isocyanate mixture was heated to 78° C. before the gradual addition of the methyl isocyanate.

Upon introduction of the isocyanate, the reaction temperature increased to 120° C. and then settled to 116°–118° C. Slight reflux was observed until 18 ml. of the isocyanate remained to be introduced. At that time, heavy reflux was observed and the temperature of the reaction started to drop. The reaction mixture was heated with heat guns in an effort to raise the temperature to the 115°-120° C. level as the remaining isocyanate was added slowly amid steady reflux. The reaction temperature continued to drop and bottomed out at 79° C. Continued efforts to heat the reaction flask raised the temperature to about 98° C.—all with heavy refluxing.

With the temperature at 98° C. and 107 minutes after the start of isocyanate addition, an additional 0.10% of pyridine was aded to the reaction flask in an attempt to complete the reaction. Thereafter, the reaction temperature increased to the 115°-120° C. in about 42 minutes. Samples were taken at 5 minutes, 30 minutes and 1 hour from the time the temperature reached the 115°-120° C. level and submitted for HPLC analysis. Results are tabulated in Table VI.

EXAMPLE XII

The procedure of Example XI was repeated except that 0.10 weight percent 4-dimethylaminopyridine was used as the catalyst. The isocyanate was added slowly over 32 minutes. A very slight amount of reflux was observed with 2 ml. of isocyanate left to be added. This reflux stopped when all of the isocyanate had been added. Samples were taken at 3 minutes, 30 minutes and 1 hour following addition of all of the isocyanate. Results are tabulated in Table VI.

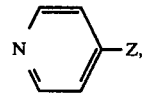

$(X)_n$ and substituted benzyl of the graphic formula:

$(Y)_m$ wherein X is halogen, $C_1$-$C_8$ alkyl, $C_1$-$C_4$ alkoxy, $C_1$-$C_4$ alkylthiol, $C_1$-$C_4$ dialkylamino, nitro, 1,3-dioxolanyl, 4,5-di($C_1$-$C_4$) alkyl-1,3-dioxolanyl, and n is an integer of from 1 to 3; Y is selected from the group consisting of halogen and nitro, and m is an integer of from 1 to 2, with an isocyanate having the graphic formula:

$$R'''-N=C=O$$

TABLE VI

| Example No. | Catalyst % | Hold Time at 115-120° C. Min. | Analysis, PCP[3] | % ALP[4] | Assay | Impurities 1[c] | 2[d] | 3[e] | 4[f] | Total 1-4 |
|---|---|---|---|---|---|---|---|---|---|---|
| XI | Pyridine,[a,b] 0.20 | | | | | | | | | |
| | | 5 | 0.31 | 0.27 | 99.1 | 0.06 | 0.11 | 0.04 | 0.08 | 0.29 |
| | | 30 | 0.37 | 0.31 | 99.1 | 0.03 | 0.11 | 0.02 | 0.07 | 0.23 |
| | | 60 | 0.02 | 0.25 | 99.5 | 0.03 | 0.11 | 0.04 | 0.07 | 0.25 |
| XII | DMAP[6], 0.10 | 3 | N.D. | 0.34 | 99.4 | 0.03 | 0.07 | 0.03 | 0.09 | 0.22 |
| | | 30 | N.D. | 0.54 | 99.3 | 0.03 | 0.06 | Trace | 0.06 | 0.15 |
| | | 64 | N.D. | 0.74 | 99.1 | 0.03 | 0.09 | 0.02 | 0.07 | 0.21 |

[a]Could not get temperature back to 115-120° C. even after 41 min. of heating with heat guns.
[b]An additional 0.10% pyridine added 107 min. after start of MIC addition. An additional 42 min. elapsed before temperature of 115° C. reached; reflux gradually diminished but did not stop.
[c]An early eluting peak which has not been identified.
[d]Carbamate of 2,6-dichlorophenol.
[e]Carbamate of 2,4-dichlorophenol.
[f]Carbamate of phenol.
[3,4,6]See Footnotes in Table 1.

The data of Table VI illustrate the difficulties encountered in controlling the reaction of p-chlorophenol and methyl isocyanate when catalyzed with pyridine alone. In addition, twice the amount of pyridine as 4-dimethylaminopyridine and almost five times the time were required to complete the reaction.

Although the present process has been described with reference to specific details of certain embodiments thereof, it is not intended that such details should be regarded as limitations upon the scope of the invention except as and to the extent that they are included in the accompanying claims.

I claim:

1. In the process of preparing aromatic esters of N-substituted carbamic acids by reaction of aromatic alcohol of the general formula, R—OH, wherein R is selected from the group consisting of phenyl, naphthyl, halosubstituted naphthyl, benzofuranyl, $C_1$-$C_4$ alkyl substituted benzofuranyl, benzyl, substituted phenyl of the graphic formula:

wherein R''' is selected from the group consisting of $C_1$-$C_3$ alkyl, phenyl and cyclohexyl, in the substantial absence of an extraneous solvent, the improvement which comprises conducting said reaction in the presence of a catalytic amount of a combination of (a) 4-aminopyridine catalyst having the graphic formula:

wherein Z is selected from the group consisting of $$-N\begin{matrix}R'\\R''\end{matrix},$$

pyrrolidino, piperidino, and morpholino, and wherein R' and R'' are each selected from the group consisting of hydrogen, $C_1$-$C_6$ alkyl and $C_3$-$C_7$ cycloalkyl, and (b)

pyridine catalyst selected from the group consisting of pyridine, methylpyridines and dimethylpyridines, the weight ratio of 4-aminopyridine catalyst to pyridine catalyst being from 5:1 to 1:5.

2. The process of claim 1 wherein between about 0.01 and about 0.5 weight percent 4-aminopyridine catalyst, based on the aromatic alcohol, is used.

3. The process of claims 1 or 2 wherein between about 0.05 and about 0.1 weight percent 4-aminopyridine catalyst, based on the aromatic alcohol, is used and the weight ratio of 4-aminopyridine catalyst to pyridine catalyst is from 2:1 to 1:2.

4. The process of claim 1 wherein the mole ratio of isocyanate to aromatic alcohol is between about 1:1 and about 1.08:1.

5. The process of claim 1 wherein the reaction temperature ranges between about 35° C. and about 150° C.

6. The process of claim 1 wherein the aromatic alcohol is represented by the graphic formula:

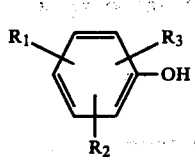

wherein $R_1$ is selected from the group consisting of hydrogen, halogen, $C_1$–$C_5$ alkyl, $C_1$–$C_3$ alkoxy, $C_1$–$C_3$-alkylthiol and nitro, and $R_2$ and $R_3$ are each selected from the group consisting of hydrogen and $C_1$–$C_5$ alkyl.

7. In the process of preparing p-chlorophenyl-N-methyl carbamate by reaction of p-chlorophenol with methyl isocyanate in the substantial absence of extraneous inert solvent, the improvement which comprises conducting said reaction in the presence of a catalytic amount of a combination of (a) 4-aminopyridine catalyst having the graphic formula:

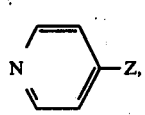

wherein Z is selected from the group consisting of

pyrrolidino, piperidino, and morpholino, and wherein R' and R" are each selected from the group consisting of hydrogen, $C_1$–$C_6$ alkyl and $C_3$–$C_7$ cycloalkyl, and (b) pyridine catalyst selected from the group consisting of pyridine, methylpyridines and dimethyl pyridines, the weight ratio of 4-aminopyridine catalyst to pyridine catalyst being from 1:1 to 2:1, thereby to produce p-chlorophenyl-N-methyl carbamate.

8. The process of claim 7 wherein between about 0.01 and about 0.1 weight percent 4-aminopyridine, based on p-chlorophenol, is used.

9. The process of claim 7 wherein between about 0.05 and about 0.075 weight percent 4-aminopyridine is used.

10. The process of claim 7 or 8 wherein the mole ratio of methyl isocyanate to p-chlorophenol is between about 1:1 and about 1.05:1.

11. The process of claim 10 wherein the 4-aminopyridine is 4-dimethylaminopyridine.

12. The process of claim 11 wherein the pyridine catalyst is pyridine and the weight ratio of 4-aminopyridine catalyst to pyridine is from about 1:1 to 1.5:1.

13. The process of claims 7 or 8 wherein the reaction temperature is between about 70° C. and about 125° C.

* * * * *